(12) United States Patent
Palumbo

(10) Patent No.: US 10,993,939 B2
(45) Date of Patent: May 4, 2021

(54) COMPOSITIONS FOR TREATING OR PREVENTING VASOMOTOR SYMPTOMS

(71) Applicant: Mitsubishi Tanabe Pharma Corporation, Osaka (JP)

(72) Inventor: Joseph M. Palumbo, Jersey City, NJ (US)

(73) Assignee: Mitsubishi Tanabe Pharmaceutical Company, Osaka (JP)

( * ) Notice: Subject to any disclaimer, the term of this patent is extended or adjusted under 35 U.S.C. 154(b) by 0 days.

(21) Appl. No.: 16/308,932

(22) PCT Filed: Jun. 12, 2017

(86) PCT No.: PCT/JP2017/021569
§ 371 (c)(1),
(2) Date: Dec. 11, 2018

(87) PCT Pub. No.: WO2017/217351
PCT Pub. Date: Dec. 21, 2017

(65) Prior Publication Data
US 2019/0142821 A1    May 16, 2019

Related U.S. Application Data

(60) Provisional application No. 62/349,179, filed on Jun. 13, 2016.

(51) Int. Cl.
*A61K 31/4725* (2006.01)
*A61P 9/14* (2006.01)
*A61K 31/472* (2006.01)
*A61K 45/06* (2006.01)

(52) U.S. Cl.
CPC ........ *A61K 31/4725* (2013.01); *A61K 31/472* (2013.01); *A61P 9/14* (2018.01); *A61K 45/06* (2013.01)

(58) Field of Classification Search
CPC ................................................ A61K 31/4725
See application file for complete search history.

(56) References Cited

U.S. PATENT DOCUMENTS

| | | | |
|---|---|---|---|
| 8,906,946 B2 | 12/2014 | Moriconi et al. | |
| 8,987,445 B2 | 3/2015 | Tsuzuki et al. | |
| 9,096,527 B2 | 8/2015 | Biswas et al. | |
| 9,487,488 B2 | 11/2016 | Kato et al. | |
| 2013/0157996 A1* | 6/2013 | Biswas | A61P 43/00 514/210.18 |
| 2014/0371276 A1 | 12/2014 | Moriconi et al. | |

FOREIGN PATENT DOCUMENTS

| | | |
|---|---|---|
| CN | 103443080 A | 12/2013 |
| CN | 103443080 A | 10/2016 |
| EP | 2 896 613 A1 | 7/2015 |
| WO | WO 2009/073788 A1 | 6/2009 |
| WO | WO 2010/080397 A1 | 7/2010 |
| WO | WO 2010/103381 A1 | 9/2010 |
| WO | WO 2010/125831 A1 | 11/2010 |
| WO | WO 2010/144680 A1 | 12/2010 |
| WO | WO-2012124825 A1 * | 9/2012 ........... C07D 409/12 |
| WO | WO 2012/177893 A2 | 12/2012 |
| WO | WO 2012/177893 A3 | 12/2012 |
| WO | WO 2014/042238 A1 | 3/2014 |
| WO | WO 2015/059432 A1 | 4/2015 |

OTHER PUBLICATIONS

Merck, Sulfonamides, 2018, Merck Manual Professional Version, https://www.merckmanuals.com/professional/infectious-diseases/bacteria-and-antibacterial-drugs/sulfonamides (Year: 2018).*
International Search Report from the European Patent Office for International Application No. PCT/JP2017/021569, dated Sep. 19, 2017.
Written Opinion of the International Searching Authority from the European Patent Office for International Application No. PCT/JP2017/021569, dated Dec. 27, 2018.
R. E. Williams et al.; "Frequency and severity of vasomotor symptoms among peri- and postmenopausal women in the United States", Climacteric, vol. 11, pp. 32-43 (2008).
Laura J. Hanisch et al.; "Increases in core body temperature precede hot flashes in a prostate cancer patient", Psycho-Oncology, vol. 18, pp. 564-567 (2009).
Karen Elkind-Hirsch; "Cooling off hot flashes: uncoupling of the circadian pattern of core body temperature and hot flash frequency in breast cancer survivors", Menopause: The Journal of the North American Menopause Society, vol. 11, No. 4, pp. 369-371 (2004).
Hadine Joffe et al.; "A Gonadotropin-Releasing Hormone Agonist Model Demonstrates That Nocturnal Hot Flashes Interrupt Objective Sleep", Sleep, vol. 36, No. 12, pp. 1977-1985 (2013).
Naseem A. Aziz et al.; Evaluation of Core and Surface Body Temperatures, Prevalence, Onset, Duration and Severity of Hot Flashes in Men after Bilateral Orchidectomy for Prostate Cancer, Int. Braz. J. Urol., vol. 34, No. 1, pp. 15-22 (2008).
McKemy et al.; "Identification of a cold receptor reveals a general role for TRP channels in thermosensation", Nature, vol. 416, No. 6876, pp. 52-58 (2002).
Abe et al.; "$Ca^{2+}$-dependent PKC activation mediates menthol-induced desensitization of transient receptor potential M8", Neuroscience Letters, vol. 397, No. 1-2, pp. 140-144 (2006).
Premkumar et al.; "Downregulation of Transient Receptor Potential Melastatin 8 by Protein Kinase C-Mediated Dephosphorylation", The Journal of Neuroscience, vol. 25, No. 49, pp. 11322-11329 (2005).

(Continued)

Primary Examiner — Kortney L. Klinkel
Assistant Examiner — Tori Strong
(74) Attorney, Agent, or Firm — Finnegan, Henderson, Farabow, Garrett & Dunner, LLP

(57) ABSTRACT

The present disclosure is directed to compositions and methods for treating or preventing vasomotor symptoms such as hot flashes, comprising a Transient Receptor Potential Melastatin 8 (TRPM8) antagonist and administering a TRPM8 antagonist, respectively.

18 Claims, 3 Drawing Sheets

(56) References Cited

OTHER PUBLICATIONS

Nonne Christelle et al.; "012: New mouse models to investigate the neurogenic erythema of skin in Rosancea subtype i", The Journal of Investigative Dermatology: Official Journal of the society for Investigative Dermatology and the European Society for Dermatological Research; 41 st Annual Meeting of the European Society for Dermatological Research, ESDR 2011, Elsevie, vol. 131, No. Suppl. 2, Sep. 1, 2011 (Sep. 1, 2011), p. S2, XP009500141, ISSN: 0022-202X, DOI: 10.1038/JID.2011.214 [retrieved on Dec. 8, 2015], Abstract 012, p. 1 (2011).

Behrendt H-J et al.; "Characterization of the mouse cold-menthol receptor TRPM8 and vanilloid receptor type-1 VR1 using a fluorometric imaging plate reader (FLIPR) assay", British Journal of Pharmacology, Wiley-Blackwell, UK, vol. 141, No. 4, Feb. 1, 2004(Feb. 1, 2004), pp. 737-745, XP002338125, ISSN: 0007-1188, DOI: 10.1038/SJ.BJP.0705652, Abstract Table 1.

Republic of Columbia, Superintendence of Industry and Commerce, Office Action No. 12195 dated Sep. 28, 2020, Columbian Patent Application No. NC2018/0013692, "Compositions for Treating or Preventing Vasomotor Symptoms".

First Office Action from National Intellectual Property Administration, P.R. China for Application No. 201780036529.0, dated Jul. 14, 2020.

Sun Jing, China Doctoral Dissertations Full-text Database, Volume of Medical and Health Science and Technology, No. 4, p. 121 (2015).

Cecil Textbook of Medicine, edited by Goldman et al., Xi'an World Publishing Corp. Ltd., pp. 2510-2511 (2015).

Goldman L. et al., China Doctoral Dissertations Full-text Database, Volume of Medical and Health Science and Technology, No. 4, p. 121 (2013).

Indonesia Patent Application No. P00201811209, Office Action dated Nov. 23, 2020.

EPC Patent Application No. 17732243.5, Office Action dated Nov. 27, 2020.

Israel Patent Application No. 262664, Office Action dated Dec. 8, 2020.

Office Action dated Jan. 11, 2021, in Mexican Patent Application No. MX/a/2018/015399.

Office Action dated Jan. 18, 2021, in Taiwanese Patent Application No. 106119449.

Nonne, Christelle et al, "New mouse models to investigate the neurogenic erythema of skin in subtype I rosacea" Journal of Investigative Dermatology, Jun. 2015.

Second Office Action dated Feb. 22, 2021, in Chinese Patent Application No. 201780036529.0.

Official Action dated Feb. 10, 2021, in Russian Patent Application No. 2019100424.

\* cited by examiner

[Fig. 1]
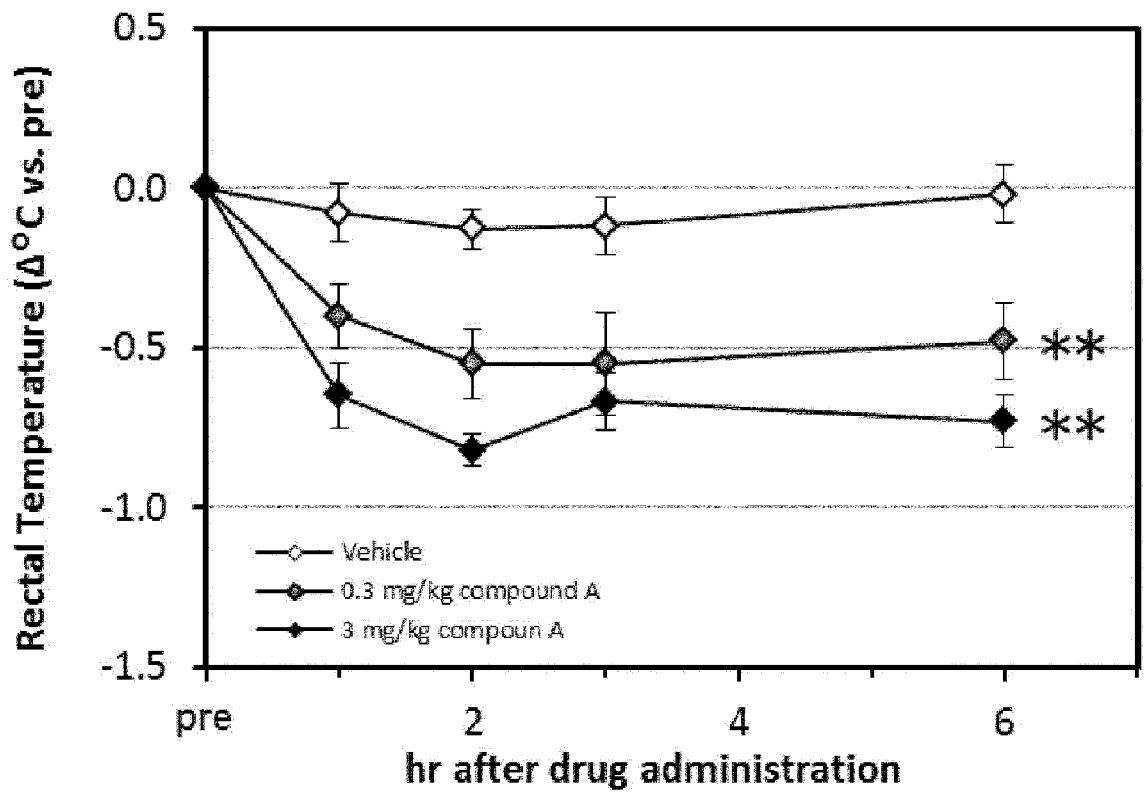
[Fig. 2]
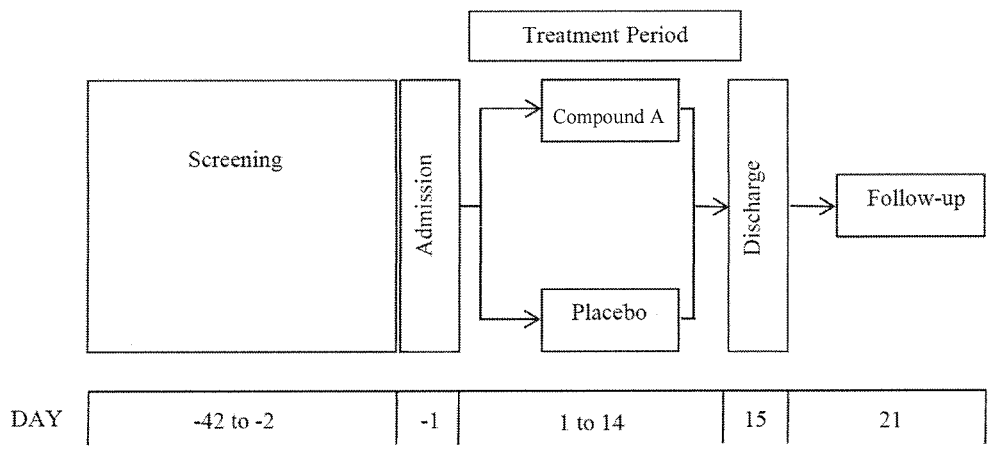

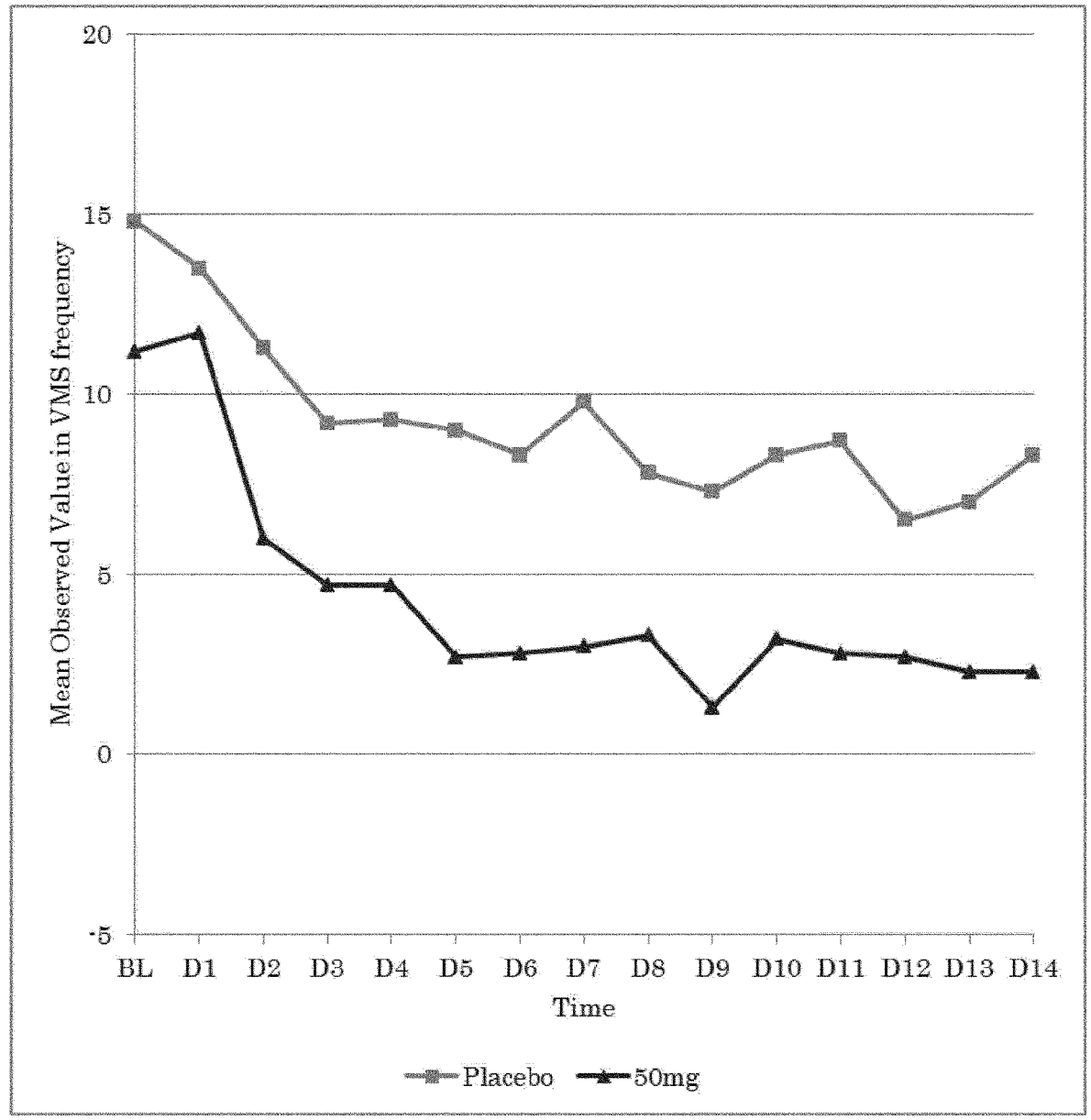

[Fig. 4]
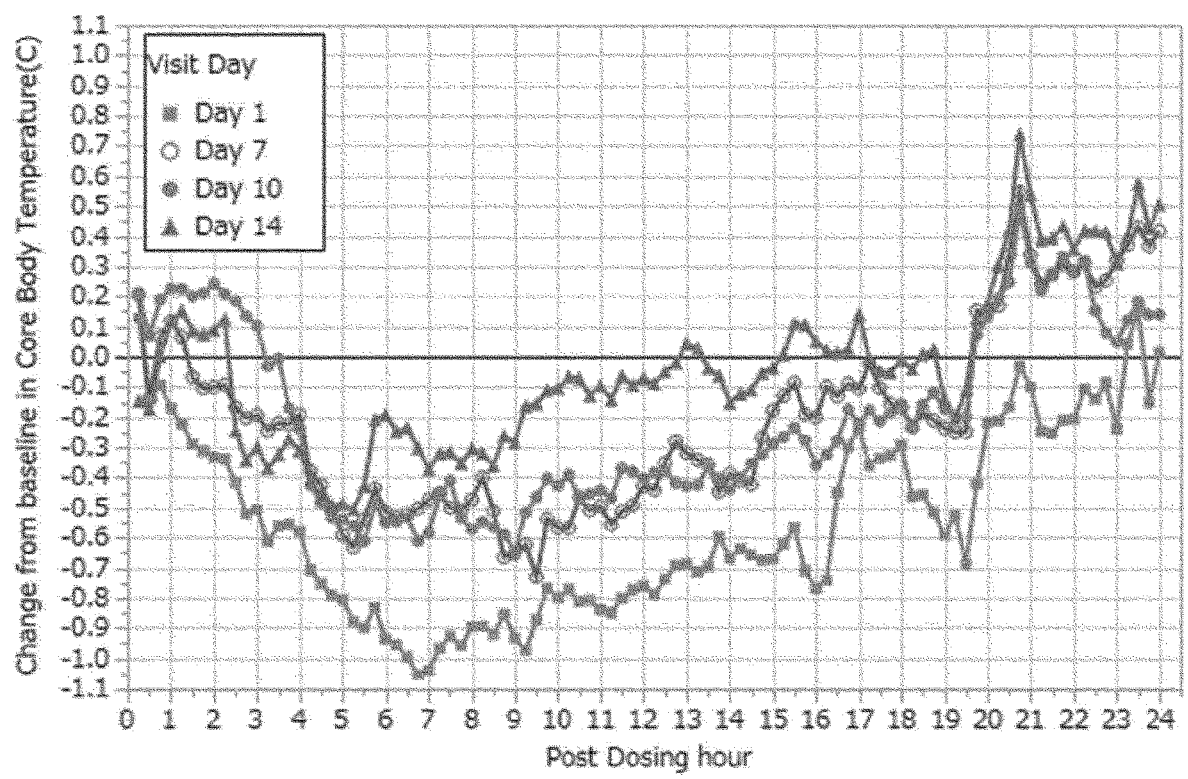

COMPOSITIONS FOR TREATING OR PREVENTING VASOMOTOR SYMPTOMS

This is a national stage application under 35 U.S.C. § 371 of International Application No. PCT/JP2017/021569, filed Jun. 12, 2017, and claims the benefit of U.S. Provisional Application No. 62/349,179, filed Jun. 13, 2016; the content of each application is incorporated herein by reference.

TECHNICAL FIELD

The present disclosure is directed to compositions and methods for treating or preventing vasomotor symptoms in a subject, comprising a Transient Receptor Potential Melastatin 8 (TRPM8) antagonist and administering a TRPM8 antagonist, respectively.

BACKGROUND ART

Vasomotor symptoms are commonly reported, e.g., symptoms of menopause. Vasomotor symptoms include night sweats, hot flashes, and flushes. The major and most common vasomotor symptoms are hot flashes. In general, hot flashes (or hot flushes or night sweats) are intermittent episodes of heat sensation. Hot flashes are the most common symptoms experienced by women who are perimenopausal or postmenopausal and are also commonly experienced by men and women who are undergoing or have undergone treatment for cancer, for example, patients receiving a breast or prostate cancer treatment that inhibits the production or activity of sex hormones. See Non-Patent Literatures 1 and 2. Studies suggest that hot flashes may be preceded by a rise in core body temperature. See Non-Patent Literature 3.

Episodes of vasomotor symptoms may also be associated with perspiration, flushing, chills, anxiety, and heart palpitations. For example, symptoms of hot flashes include a sudden sensation of warmth, often accompanied by one or more of sweating, skin reddening or flushing, and sensations of clamminess and chills. Hot flashes can be characterized by brief, mild warmth to waves of heat and profuse sweating. Typical hot flashes occur with sudden onsets of sensation of warmth in the chest, which then spreads upward to involve the neck and face and may also spread throughout the body. Others may feel a sudden onset of warmth all over the upper part of the body. Hot flashes may also be accompanied by dizziness, nausea, headaches, and palpitations. Hot flashes accompanied with sweating can also occur at night. These are called night sweats and have been linked to chronic insomnia and poor subjective sleep quality. See Non-Patent Literature 4. Recent polysomnography studies have determined that hot flashes occurring at night correlate with increased sleep fragmentation, which can result in, e.g., sleep deprivation, fatigue, and irritability. Thus, hot flashes can disrupt sleep and work and interfere with quality of life.

The severity of vasomotor symptoms varies from person to person and from time to time in the same person. For example, hot flashes can be provoked by several factors, such as hot weather, stress, eating, drinking alcohol, hormone changes, a medical condition, or medical treatment. Episodes can last from a few seconds to several minutes or in rarer cases up to an hour or more. Vasomotor symptoms can occur from several times a year to several times a week to as frequently as one or more per hour.

Hot flashes have been studied extensively in perimenopausal and postmenopausal women. Studies have shown that about 60% to 80% of women experience hot flashes in the period within peri- and postmenopause. Within this population, 40% to 60% report moderate-to-severe hot flashes, and 10% to 20% find them nearly intolerable. Thus, there is a need for effectively treating or preventing vasomotor symptoms (e.g., hot flashes) to maintain the quality of life of many women.

Vasomotor symptoms may also be experienced by both men and women as a symptom of a medical condition or a symptom of treatment. For example, vasomotor symptoms are experienced by many cancer patients as a symptom of the cancer or a symptom of the cancer treatment.

For instance, men with prostate cancer who undergo androgen deprivation therapy (ADT) may have hot flashes. This is a major quality of life issue for a significant proportion of men receiving ADT. It has been reported that about 40% to 80% of such men suffer hot flashes and 30% to 40% report major discomfort during such episodes. See Non-Patent Literature 5.

There are several known treatments for vasomotor symptoms; however, current treatments are not completely effective and may confer increased risk of serious complications. Although estrogen replacement therapy can effectively minimize or prevent vasomotor symptoms in women, many women are concerned about potential risks of hormone replacement therapy. This is especially true for women who suffer from breast cancer or have a family history of breast cancer, and/or a history of clotting disorders. Selective serotonin reuptake inhibitors (SSRIs), serotonin and norepinephrine reuptake inhibitors (SNRIs), gabapentin and clonidine may also be used for the treatment of vasomotor symptoms, but are not always effective at treating symptoms and many are associated with unwanted side effects.

CITATION LIST

Non Patent Literature

[NPL 1] R. E. Williams et al., "Frequency and severity of vasomotor symptoms among peri- and postmenopausal women in the United States," Climacteric, 11:32-43 (2008)

[NPL 2] Laura J. Hanisch et al., "Increases in core body temperature precede hot flashes in a prostate cancer patient," Psycho-Oncology, 18:564-567 (2009)

[NPL 3] Karen Elkind-Hirsch, "Cooling off hot flashes: uncoupling of the circadian pattern of core body temperature and hot flash frequency in breast cancer survivors," Menopause: The Journal of The North American Menopause Society, Vol. 11, No. 4, pp. 369-371 (2004)

[NPL 4] Hadine Joffe et al., "A Gonadotropin-Releasing Hormone Agonist Model Demonstrates That Nocturnal Hot Flashes Interrupt Objective Sleep," Sleep, Vol. 36, No. 12, pp. 1977-1985 (2013).

[NPL 5] Naseem A. Aziz, "Evaluation of Core and Surface Body Temperatures, Prevalence, Onset, Duration and Severity of Hot Flashes in Men after Bilateral Orchidectomy for Prostate Cancer," Int. Braz. J. Urol., 34:15-22 (2008)

SUMMARY OF INVENTION

Technical Problem

Thus, there is a need for new safe and effective treatments for vasomotor symptoms. The present inventors discovered a new treatment for vasomotor symptoms by administering an active agent that is a transient receptor potential melastatin-8 (TRPM8) antagonist.

Transient receptor potential (TRP) channels are non-selective cation channels that are activated by a variety of physical (e.g., temperature, osmolarity, mechanical) and chemical stimuli. A subset of the TRP channel superfamily is thermoresponsive, each channel activated over a discrete temperature range, cumulatively spanning from noxious cold to noxious heat. TRPM8 belongs to the melastatin subgroup of the TRP channel superfamily. TRPM8 is sensitive to cold temperature and menthol, and thus is also called the cold and menthol receptor-1 (CMR-1). McKemy et al., "Identification of a cold receptor reveals a general role for TRP channels in thermosensation," Nature, Vol. 416, No. 6876, pp. 52-58 (2002). TRPM8 is known to be stimulated by cool to cold temperatures (8 to 28° C.) as well as by chemical substances such as menthol and icilin.

TRPM8 is located on primary nociceptive neurons (A-$\delta$ and C-fibers) and is also modulated by inflammation-mediated second messenger signals. Abe et al., "Ca2±-dependent PKC activation mediates menthol-induced desensitization of transient receptor potential M8," Neuroscience Letters, Vol. 397, No. 1-2, p. 140-144 (2006); Premkumar et al., "Down-regulation of Transient Receptor Potential Melastatin 8 by Protein Kinase C-Mediated Dephosphorylation," The Journal of Neuroscience, Vol. 25, No. 49, p. 11322-11329 (2005). TRPM8 is highly expressed in sensory neurons of the trigeminal and dorsal root ganglia. TRPM8 is also known to be expressed in the brain, lung, bladder, gastrointestinal tract, blood vessels, prostate, and immune cells.

TRPM8 antagonists and their use in treatments have been disclosed in previous patent filings (see, e.g., U.S. Pat. Nos. 8,987,445; 9,096,527; International Patent Publication No. WO 2014/042238). These disclosures report uses such as for the treatment of chronic pain (e.g., neuropathic pain), urologic disease, gastrointestinal disease, and cephalalgia. None of these disclosures, however, describe treating or preventing vasomotor symptoms with a TRPM8 antagonist.

Solution to Problem

The present disclosure is directed to a method for treating or preventing vasomotor symptoms in a subject in need thereof, comprising administering to the subject an effective amount of a TRPM8 antagonist.

The present disclosure is also directed to a composition comprising an effective amount of a TRPM8 antagonist for treating or preventing vasomotor symptoms in a subject and a pharmaceutically acceptable carrier.

The accompanying drawings are incorporated in and constitute a part of this specification.

BRIEF DESCRIPTION OF DRAWINGS

FIG. 1 shows the effect on rectal temperature in rats of administering a TRPM8 antagonist (in particular Compound A as described herein).

FIG. 2 shows the study design of a planned Phase I, randomized, double-blind, placebo-controlled study to assess the safety, tolerability and pharmacokinetics of multiple doses of Compound A as described herein in female subjects experiencing vasomotor symptoms.

FIG. 3 shows a change in Mean observed value in Vasomotor Symptoms (VMS) frequency over time within 24-hour after the first dose during the 14 days of treatment period. In the FIG. 3, each of the triangle or square symbol shows the result for 50 mg of Compound A or Placebo, respectively.

FIG. 4 shows a change from baseline in core body temperature over time within 24 hour post-dose on the Visit Day 1, 7, 10 or 14. In the FIG. 4, each of square, triangle, open circle, or closed circle symbol shows the results on the Visit Day 1, 7, 10 or 14, respectively.

DESCRIPTION OF EMBODIMENTS

Description

It is to be understood that both the foregoing general description and the following detailed description are exemplary and explanatory only and are not restrictive of the invention, as claimed. It should also be understood that the present disclosure is not limited to specific active agents, formulations, dosing regimens, and the like, as such may vary.

Particular aspects of the disclosure are described in greater detail below. The terms and definitions as used in the present application and as clarified herein are intended to represent the meaning within the present disclosure.

As used herein, the singular forms "a," "an," and "the" include plural reference unless the context dictates otherwise.

The terms "approximately" and "about" mean to be nearly the same as a referenced number or value, including an acceptable degree of error for the quantity measured given the nature or precision of the measurements. As used herein, the terms "approximately" and "about" should be generally understood to encompass ±20% of a specified amount, frequency or value. Numerical quantities given herein are approximate unless stated otherwise, meaning that term "about" or "approximately" can be inferred when not expressly stated. "Vasomotor symptoms," as used herein, are known in the art and include all hot flashes, whether mild, moderate, or severe. Vasomotor symptoms may also include, but are not limited to, night sweats and flushes.

"Hot flashes" as used herein refers to episodic sensations of heat, optionally accompanied by flushing and sweating, also optionally accompanied by tachycardia and chills. "Hot flash" as used herein may refer to hot flashes associated with menopause, with the symptoms or effects of a medical condition, with the side effects of a treatment for a medical condition, e.g., as a side effect of cancer treatment, or with any other triggers or causes of hot flashes. The term also includes "hot flushes." "Night sweats" are hot flashes that occur during sleep.

The term "active agent" refers to a chemical compound that induces a desired effect. The present disclosure is directed to TRPM8 antagonists, although combination therapy wherein a TRPM8 antagonist is administered with one or more additional active agents is also within the scope of the present disclosure. Such combination therapy may be carried out by administration of the different active agents in a single composition, by concurrent administration of the different active agents in different compositions, or by sequential administration of the different active agents. Derivatives and analogs of the active agents and classes of active agents disclosed herein that induce the desired effect are within the scope of the present disclosure.

As used herein, a "Transient Receptor Potential Melastatin 8 (TRPM8) antagonist" is any compound that, upon administration to an individual, has or converts to a metabolite that has TRPM8 antagonistic activity, whether selective or non-selective.

"Treating" or "preventing" vasomotor symptoms or the "treatment" or "prevention" of vasomotor symptoms as used herein includes one or more of (1) reducing, minimizing, or eliminating the occurrence or frequency of vasomotor symptoms; (2) relieving vasomotor symptoms when they occur; (3) reducing or minimizing the severity of (or palliating) or eliminating one or more symptoms of vasomotor symptoms; and (4) delaying the progression or development of vasomotor symptoms. The compositions and methods described herein may treat or prevent vasomotor symptoms (e.g., hot flashes) that occur at night (i.e., night sweats). In these embodiments, treating or preventing as described herein may also include reducing time to initial onset of sleep, increasing total sleep time, reducing the number of sleep disturbances or awakenings, and increasing the deeper levels of sleep.

As used herein, a "subject" may be a human or an animal.

As used herein, "core body temperature" refers to the internal body temperature of a subject. Core body temperature can be measured using techniques known in the art. In some embodiments, invasive means are used, such as placing a temperature probe into the oesophagus, pulmonary artery, or urinary bladder. In some embodiments, core body temperature is measured at a digestive organ. In some embodiments, core body temperature is measured at noninvasive sites, such as the rectum, oral cavity, axilla, temporal artery, or external auditory canal. In some embodiments, core body temperature is consistently measured at the same site, e.g., when evaluating the occurrence and/or extent of a decrease in core body temperature of a subject.

The term "administer," "administration," or "administering" means the step of providing, giving, dosing and/or prescribing a drug according to the disclosure to an individual, or the step of an individual receiving, applying, taking, and/or consuming a drug according to the disclosure. The route of administration of an active agent or composition according to the present disclosure may be by any route of administration, for example, oral, parenteral, transmucosal, intranasal, inhalation, or transdermal.

An "effective amount" as used herein refers to an amount of a compound sufficient to provide the desired effect, i.e., in this case, the treatment or prevention of vasomotor symptoms as described herein. Additionally, "effective amount" may also refer to an amount of a compound that provides the desired effect without adding or increasing an undesired effect, i.e., an unwanted side effect. In certain embodiments, the effective amount of a TRPM8 antagonist is chosen to target the treatment or prevention of vasomotor symptoms (e.g., hot flashes) that occur at night (i.e., night sweats) as described herein. As is understood in the clinical context, the administration of an amount of a drug, compound, or composition may be coupled with the administration of another drug, compound, or composition. Thus, an "effective amount" may be considered in the context of administering one or more active agents, and a single agent may be considered to be given in an effective amount if, in conjunction with one or more other agents, a desirable result may be or is achieved.

"Pharmaceutically acceptable" as used herein means a material that is not biologically or otherwise undesirable. That is, the material may be incorporated into a composition administered to an individual without causing undesirable biological effects or interacting in a deleterious manner with other components of the composition in which it is contained.

A "perimenopausal woman" refers to a woman within the interval in which the woman's body makes a shift from more-or-less regular cycles of ovulation and menstruation toward permanent infertility or menopause. The interval may be a period of a few months, to several years, to 15 years or more before menopause. "Perimenopause" is also known as the menopausal transition. A "postmenopausal woman" refers to a woman who has undergone menopause, i.e., experienced twelve consecutive months without menstruation. A "menopausal woman" as used herein includes both a perimenopausal woman and a postmenopausal woman as defined herein. The menopause in these women may be either natural (such as with age), surgical (such as by removal of both ovaries), or induced by chemical treatment (such as by treatment with estrogen antagonists, e.g. fulvestrant, raloxifene, tamoxifen, or toremifene).

The present inventors discovered a new treatment for vasomotor symptoms by administering an active agent that is a TRPM8 antagonist. Without wishing to be bound by any particular theory, the present inventors believe that TRPM8 antagonists utilize the body's methods of passive cooling to prospectively reduce core body temperature. In use, the present inventors believe that TRPM8 antagonists will rebalance sensory input, allowing a new equilibration to a slightly lower, and newly stabilized, but still normal, core body temperature. The body's need for excessive thermoregulatory shifts will be prevented and heat that would otherwise have been shifted to the skin surface in a hot flash will tend to be made unnecessary.

The present disclosure is directed to a method for treating or preventing vasomotor symptoms in a subject in need thereof, comprising administering to the subject an effective amount of a TRPM8 antagonist. In some embodiments, the vasomotor symptom is hot flashes. In some embodiments, the subject is a human. The subject may be male or female. It is envisioned that the methods will be used for subjects that are prone to having, are having, or are expected to have vasomotor symptoms, such as hot flashes. The subject in need thereof may suffer from or anticipate suffering from vasomotor symptoms associated with menopause, with the symptoms or effects of a medical condition, with the side effects of a treatment for a medical condition, or with any other trigger or cause of vasomotor symptoms.

Subjects include, but are not limited to, menopausal women, subjects who are taking or anticipate taking antiestrogen drugs (such as tamoxifen or aromatase inhibitors), subjects who are anticipating or have gone through surgery, or subjects having or anticipating having any other condition or undergoing or anticipating undergoing any other treatment that results in changes in hormone levels.

Subjects further include, but are not limited to, oncology patients. For example, subjects may include those who are anticipating, are undergoing, or have undergone cancer treatment, such as through surgery or radiation therapy. For example, subjects may include those who are anticipating, are undergoing, or have undergone gonadal ablative therapy or gonadal hormonal suppressive therapy. Where the subject is undergoing or has undergone cancer treatment, the cancer treatment can be a treatment which affects the hormone levels of the subject, for example, hormonal therapy treatment for breast cancer, ovarian cancer and prostate cancer. Examples of hormonal therapies for cancers include: selective estrogen receptor antagonists including tamoxifen (Nolvadex (registered trademark)), raloxifene (Evista (registered trademark)), lasofoxifene (Fablyn) and toremifene (Fareston (registered trademark)); antiestrogen drugs including fulvestrant (Faslodex (registered trademark)); aromatase inhibitors including anastrozole (Arimidex (registered trademark)), letrozole (Femara (registered trademark)), vorozole (Rivizor), formestane (Lentaron), fadrozole (Afema) and exemestane (Aromasin (registered trademark)); luteinizing-hormone-releasing hormone (LHRH) agonists including goserelin (Zoladex (registered trademark)), leuprolide (Lupron (registered trademark)); luteinising hormone (LH) blockers including buserelin, leuprorelin (Prostap (registered trademark)), histrelin (Vantas (registered trademark)), deslorelin (Suprelorin (registered trademark)), nafarelin (Synarel (registered trademark)) and triptorelin (Decapeptyl (registered trademark)); anti androgens including flutamide (Drogenil (registered trademark)), nilutamide (Nilandron (USA)/Anandron (Canada)) and bicalutamide (Casodex (registered trademark)); gonadotrophin releasing hormone (GnRH) blocker including degarelix (Firmagon (registered trademark)); and abiraterone (Zytiga (registered trademark)).

Subjects also include, but are not limited to, subjects who are anticipating or have gone through surgically-induced hormonal variations, such as hysterectomy, oophorectomy, and orchiectomy.

The effective amount of a TRPM8 antagonist may be administered as a composition comprising the TRPM8 antagonist and a pharmaceutically acceptable carrier. In certain embodiments, the composition is a pharmaceutical composition.

Administration of an effective amount of a TRPM8 antagonist or composition thereof may be on an as-needed basis or may be on a schedule, such as in an ongoing dosing regimen. For example, the effective amount may be administered as needed, such as immediately upon sensing the onset of vasomotor symptoms, such as a hot flash. Scheduled administration may be on a uniform schedule or on a non-uniform schedule where the frequency of administration is correlated with the circadian rhythm of vasomotor symptoms, either in the symptomatic population or of the individual treated. Even if scheduled administration is used, it is possible to administer the compound on an as-needed basis if vasomotor symptoms are still experienced. In some embodiments, the effective amount of a TRPM8 antagonist or composition thereof is administered daily, such as once daily or twice daily. In some embodiments, the timing and frequency of administration is chosen to target the treatment or prevention of vasomotor symptoms (e.g., hot flashes) that occur at night (i.e., night sweats) as described herein. In certain embodiments, the effective amount of a TRPM8 antagonist or composition thereof is administered in the evening, such as a dosing regimen comprising once daily administration in the evenings. In some embodiments, the effective amount of a TRPM8 antagonist or composition thereof is administered before bedtime, such as a dosing regimen comprising once daily administration before bedtime.

The administration of the TRPM8 antagonist or composition thereof is not limited to any particular route of administration, such as oral administration.

The TRPM8 antagonist of the present disclosure is not limited to any particular compound or class of compounds. Compounds and classes of compounds not specifically mentioned but that exhibit TRPM8 antagonistic activity are within the scope of the present disclosure. Examples of TRPM8 antagonists include, but are not limited to, sulfonamides (U.S. Pat. No. 8,987,445), sulfamides (WO2010/080397), amides (U.S. Pat. No. 9,096,527), 2-aryl oxazoles (US2014/0371276), 2-aryl thiazoles (US2014/0371276), spirocyclic piperidines (WO2010/103381), naphthyl derivatives (U.S. Pat. No. 8,906,946), and benzimidazole derivatives (WO2010/144680), the disclosures of which are hereby incorporated by reference in their entirety. For example, the TRPM8 antagonist may be chosen from sulfonamide compounds. In some embodiments, the sulfonamide compound is represented by the following formula (I):

[Chem.1]

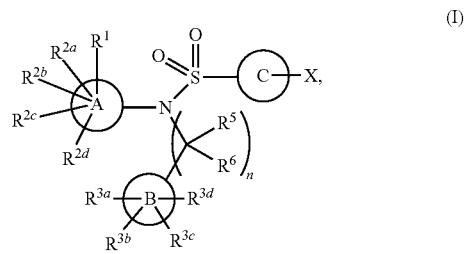

(I)

wherein:

Ring A is bicyclic aromatic heterocycle comprised of (a) pyridine condensed with benzene; or (b) pyridine condensed with 5 to 6-membered monocyclic aromatic heterocycle containing carbon atoms and 1 to 4 heteroatoms selected from oxygen atom, sulfur atom and nitrogen atom, and Ring A binds to a sulfonylamino moiety on a carbon atom adjacent to a nitrogen atom of pyridine ring constituting Ring A, Ring B is (a) monocyclic or bicyclic aromatic hydrocarbon with 6 to 11 carbons as a ring atom; (b) monocyclic or bicyclic alicyclic hydrocarbon with 3 to 12 carbons as a ring atom; (c) 5 to 11-membered monocyclic or bicyclic aromatic heterocycle containing carbon atoms and 1 to 4 heteroatoms selected from oxygen atom, sulfur atom and nitrogen atom; or (d) 4 to 12-membered monocyclic or bicyclic non-aromatic heterocycle containing carbon atoms and 1 to 4 heteroatoms selected from oxygen atom, sulfur atom and nitrogen atom, Ring C is (a) benzene; or (b) 5 to 6-membered monocyclic aromatic heterocycle containing carbon atoms and 1 to 4 heteroatoms selected from oxygen atom, sulfur atom and nitrogen atom, $R^1$ is (a) hydrogen; (b) $C_1$-$C_6$ alkyl which may be optionally substituted by 1 to 7 groups selected from $C_3$-$C_7$ cycloalkyl, $C_1$-$C_6$ alkoxy, halogen, oxo and hydroxy; (c) $C_3$-$C_7$ cycloalkyl which may be optionally substituted by 1 to 7 groups selected from $C_1$-$C_6$ alkyl, $C_1$-$C_6$ alkoxy and halogen; (d) $C_1$-$C_6$ alkoxy which may be optionally substituted by 1 to 7 groups selected from $C_3$-$C_7$ cycloalkyl, $C_1$-$C_6$ alkoxy, halogen and hydroxy; (e) phenyl which may be optionally substituted by 1 to 3 groups selected from $C_1$-$C_6$ alkyl, $C_1$-$C_6$ halogenoalkyl, $C_3$-$C_7$ cycloalkyl, $C_3$-$C_7$ halogenocycloalkyl, $C_1$-$C_6$ alkoxy, $C_1$-$C_6$ halogenoalkoxy and halogen; (f) halogen; or (g) nitrile, $R^{2a}$, $R^{2b}$, $R^{2c}$ and $R^{2d}$ are each independently (a) hydrogen; (b) $C_1$-$C_6$ alkyl which may be optionally substituted by 1 to 7 groups selected from $C_1$-$C_6$ alkoxy, $C_3$-$C_7$ cycloalkyl, halogen, oxo and hydroxy; (c) $C_3$-$C_7$ cycloalkyl which may be optionally substituted by 1 to 7 groups selected from $C_1$-$C_6$ alkyl, $C_1$-$C_6$ alkoxy and halogen; (d) $C_1$-$C_6$ alkoxy which may be optionally substituted by 1 to 7 groups selected from $C_1$-$C_6$ alkoxy, $C_3$-$C_7$ cycloalkyl and halogen; (e) phenyl which may be optionally substituted by 1 to 3 groups selected from $C_1$-$C_6$ alkyl, $C_1$-$C_6$ halogenoalkyl, $C_3$-$C_7$ cycloalkyl, $C_3$-$C_7$ halogenocycloalkyl, $C_1$-$C_6$ alkoxy, $C_1$-$C_6$ halogenoalkoxy and halogen; (f) 5 to 6-membered monocyclic aromatic heterocyclic group which may be optionally substituted by 1 to 3 groups selected from $C_1$-$C_6$ alkyl, $C_1$-$C_6$ halogenoalkyl, $C_3$-$C_7$ cycloalkyl, $C_3$-$C_7$ halogenocycloalkyl, $C_1$-$C_6$ alkoxy, $C_1$-$C_6$ halogenoalkoxy and halogen; (g) 4 to 7-membered monocyclic non-aromatic heterocyclic group which may be optionally substituted by 1 to 3 groups selected from $C_1$-$C_6$ alkyl, $C_1$-$C_6$ halogenoalkyl, $C_3$-$C_7$ cycloalkyl, $C_3$-$C_7$ halogenocycloalkyl, $C_1$-$C_6$ alkoxy, $C_1$-$C_6$ halogenoalkoxy and halogen; (h) halogen; or (i) nitrile, $R^{3a}$, $R^{3b}$, $R^{3c}$ and $R^{3d}$ are each independently (a) hydrogen; (b) $C_1$-$C_6$ alkyl which may be optionally substituted by 1 to 7 groups selected from $C_3$-$C_7$ cycloalkyl, $C_3$-$C_7$ halogenocycloalkyl (in which the cycloalkyl and halogenocycloalkyl may be each independently optionally substituted by 1 to 3 groups selected from $C_1$-$C_6$ alkyl and $C_1$-$C_6$ halogenoalkyl), $C_1$-$C_6$ alkoxy, $C_1$-$C_6$ halogenoalkoxy, phenyl, 5 to 6-membered monocyclic aromatic heterocyclic group, 4 to 7-membered monocyclic non-aromatic heterocyclic group (in which the phenyl, aromatic heterocyclic group and non-aromatic heterocyclic group may be each independently optionally substituted by 1 to 3 groups selected from $C_1$-$C_6$ alkyl, $C_1$-$C_6$ halogenoalkyl, $C_3$-$C_7$ cycloalkyl, $C_3$-$C_7$ halogenocycloalkyl, $C_1$-$C_6$ alkoxy, $C_1$-$C_6$ halogenoalkoxy and halogen), halogen, oxo and hydroxy; (c) $C_3$-$C_7$ cycloalkyl which may be optionally substituted by 1 to 7 groups selected from $C_1$-$C_6$ alkyl, $C_1$-$C_6$ halogenoalkyl, $C_1$-$C_6$ alkoxy, $C_1$-$C_6$ halogenoalkoxy, halogen and hydroxy; (d) $C_1$-$C_6$ alkoxy which may be optionally substituted by 1 to 7 groups selected from $C_3$-$C_7$ cycloalkyl, $C_3$-$C_7$ halogenocycloalkyl (in which the cycloalkyl and halogenocycloalkyl may be each independently optionally substituted by 1 to 3 groups selected from $C_1$-$C_6$ alkyl and $C_1$-$C_6$ halogenoalkyl), $C_1$-$C_6$ alkoxy, $C_1$-$C_6$ halogenoalkoxy, phenyl, 5 to 6-membered monocyclic aromatic heterocyclic group, 4 to 7-membered monocyclic non-aromatic heterocyclic group (in which the phenyl, aromatic heterocyclic group and non-aromatic heterocyclic group may be each independently optionally substituted by 1 to 3 groups selected from $C_1$-$C_6$ alkyl, $C_1$-$C_6$ halogenoalkyl, $C_3$-$C_7$ cycloalkyl, $C_3$-$C_7$ halogenocycloalkyl, $C_1$-$C_6$ alkoxy, $C_1$-$C_6$ halogenoalkoxy and halogen), halogen and hydroxy; (e) $C_3$-$C_7$ cycloalkoxy which may be optionally substituted by 1 to 7 groups selected from $C_1$-$C_6$ alkyl, $C_1$-$C_6$ halogenoalkyl, $C_1$-$C_6$ alkoxy, $C_1$-$C_6$ halogenoalkoxy, halogen and hydroxy; (f) phenyl which may be optionally substituted by 1 to 3 groups selected from $C_1$-$C_6$ alkyl, $C_1$-$C_6$ halogenoalkyl, $C_3$-$C_7$ cycloalkyl, $C_3$-$C_7$ halogenocycloalkyl, $C_1$-$C_6$ alkoxy, $C_1$-$C_6$ halogenoalkoxy and halogen; (g) 5 to 6-membered monocyclic aromatic heterocyclic group which may be optionally substituted by 1 to 3 groups selected from $C_1$-$C_6$ alkyl, $C_1$-$C_6$ halogenoalkyl, $C_3$-$C_7$ cycloalkyl, $C_3$-$C_7$ halogenocycloalkyl, $C_1$-$C_6$ alkoxy, $C_1$-$C_6$ halogenoalkoxy and halogen; (h) 4 to 7-membered monocyclic non-aromatic heterocyclic group which may be optionally substituted by 1 to 3 groups selected from $C_1$-$C_6$ alkyl, $C_1$-$C_6$ halogenoalkyl, $C_3$-$C_7$ cycloalkyl, $C_3$-$C_7$ halogenocycloalkyl, $C_1$-$C_6$ alkoxy, $C_1$-$C_6$ halogenoalkoxy and halogen; (i) phenoxy which may be optionally substituted by 1 to 3 groups selected from $C_1$-$C_6$ alkyl, $C_1$-$C_6$ halogenoalkyl, $C_3$-$C_7$ cycloalkyl, $C_3$-$C_7$ halogenocycloalkyl, $C_1$-$C_6$ alkoxy, $C_1$-$C_6$ halogenoalkoxy and halogen; (j) halogen; or (k) hydroxy, or two substituent groups selected from $R^{3a}$, $R^{3b}$, $R^{3c}$ and $R^{3d}$ combine each other to form oxo, $R^5$ and $R^6$ are each independently (a) hydrogen; (b) $C_1$-$C_6$ alkyl; (c) $C_1$-$C_6$ halogenoalkyl; (d) $C_3$-$C_7$ cycloalkyl; or (e) $C_3$-$C_7$ halogenocycloalkyl, or $R^5$ and $R^6$ combine each other at their terminals together with the adjacent carbon atom to form 3 to 7-membered monocyclic alicyclic hydrocarbon, n is 0, 1 or 2;

X is (a) carboxy; (b) $C_1$-$C_6$ alkoxycarbonyl; (c) hydroxy-$C_1$-$C_6$ alkyl; (d) aminocarbonyl wherein a nitrogen atom may be optionally substituted by one group selected from $C_1$-$C_6$ alkyl, $C_1$-$C_6$ alkoxy and nitrile; or (e) $C_2$-$C_7$ alkanoyl which may be optionally substituted by 1 to 3 halogens; or a pharmaceutically acceptable salt thereof.

In an embodiment of the sulfonamide compound, a partial structure of formula:

[Chem.2]

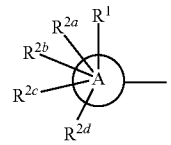

is a group of formula:

[Chem.3]

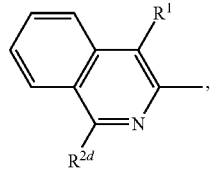

Ring B is benzene or pyridine, and a partial structure of formula:

[Chem.4]

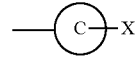

is a group of formula:

[Chem.5]

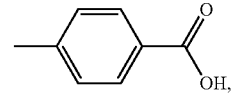

wherein
$R^1$ is (a) $C_1$-$C_6$ alkyl which may be optionally substituted by 1 to 7 halogens; (b) $C_3$-$C_7$ cycloalkyl; (c) $C_1$-$C_6$ alkoxy; or (d) halogen, $R^{2d}$ is (a) hydrogen; (b) $C_1$-$C_6$ alkyl which may be optionally substituted by 1 to 7 halogens; (c) $C_3$-$C_7$ cycloalkyl; or (d) $C_1$-$C_6$ alkoxy, $R^{3a}$ and $R^{3b}$ are each independently (a) hydrogen; (b) $C_1$-$C_6$ alkyl which may be optionally substituted by 1 to 7 groups selected from $C_3$-$C_7$ cycloalkyl (in which the cycloalkyl may be optionally substituted by 1 to 3 groups selected from $C_1$-$C_6$ alkyl and $C_1$-$C_6$ halogenoalkyl), $C_1$-$C_6$ alkoxy, $C_1$-$C_6$ halogenoalkoxy, and halogen; (c) $C_3$-$C_7$ cycloalkyl which may be optionally substituted by 1 to 7 groups selected from $C_1$-$C_6$ alkyl, $C_1$-$C_6$ halogenoalkyl, and halogen; (d) $C_1$-$C_6$ alkoxy which may be optionally substituted by 1 to 7 groups selected from $C_3$-$C_7$ cycloalkyl, $C_1$-$C_6$ alkoxy, $C_1$-$C_6$ halogenoalkoxy, and halogen; or (e) halogen, $R^{3c}$ and $R^{3d}$ are hydrogen,
$R^5$ and $R^6$ are hydrogen,
n is 1;
or a pharmaceutically acceptable salt thereof.

In certain embodiments, the sulfonamide compound is selected from the group consisting of:
4-({(1-cyclopropyl-4-methylisoquinolin-3-yl)[4-(trifluoromethoxy)benzyl]amino}sulfonyl)benzoic acid,
4-({(1-isopropyl-4-methylisoquinolin-3-yl)[4-(trifluoromethoxy)benzyl]amino}sulfonyl)benzoic acid,
4-{[{3-chloro-4-[cyclopropyl(difluoro)methyl]benzyl}(4-methylisoquinolin-3-yl)amino]sulfonyl}benzoic acid,
4-({(4-cyclopropylisoquinolin-3-yl)[4-(trifluoromethoxy)benzyl]amino}sulfonyl)benzoic acid,
4-{[{3-chloro-4-[cyclopropyl(difluoro)methyl]benzyl}(1-cyclopropyl-4-methylisoquinolin-3-yl)amino]sulfonyl}benzoic acid,
4-{[{4-[cyclopropyl(difluoro)methyl]-3-fluorobenzyl}(4-methylisoquinolin-3-yl)amino]sulfonyl}benzoic acid,
4-({[4-(trifluoromethoxy)benzyl][4-(trifluoromethyl)isoquinolin-3-yl]amino}sulfonyl)benzoic acid,
4-[((4-cyclopropylisoquinolin-3-yl){[5-(trifluoromethyl)pyridin-2-yl]methyl}amino)sulfonyl]benzoic acid,
4-{[{4-[cyclopropyl(difluoro)methyl]-3-fluorobenzyl}(4-cyclopropylisoquinolin-3-yl)amino]sulfonyl}benzoic acid; and
a pharmaceutically acceptable salt thereof.

In certain embodiments, the sulfonamide compound is a compound having the formula:

[Chem.6]

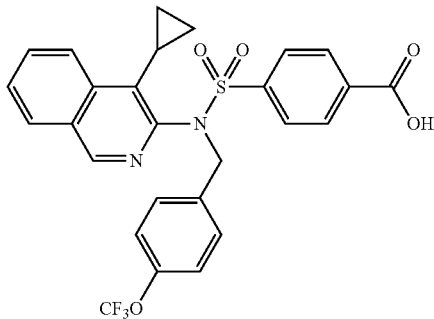

(i.e., 4-({(4-cyclopropylisoquinolin-3-yl)[4-(trifluoromethoxy)benzyl]amino}sulfonyl)benzoic acid) (hereinafter referred to as "Compound A");
or a pharmaceutically acceptable salt thereof.

The sulfonamide compounds of formula (I) can be synthesized by methods known to a skilled artisan. Some of those methods are described in e.g., U.S. Pat. Nos. 8,987,445 and 9,096,527 and International Patent Publication No. WO 2014/042238.

Although the precise mechanism of action is not completely understood, it is known that these sulfonamide compounds do not work by the same mechanisms as most other known treatments for vasomotor symptoms. As such, the sulfonamide compounds are suitable for use as a sole or additional treatment for treating or preventing vasomotor symptoms or in combination with other active agents known to produce vasomotor symptoms as a side effect so as to minimize or eliminate this side effect. In some embodiments, the TRPM8 antagonist is chosen from sulfonamide compounds represented by formula (I), such as Compound A or a pharmaceutically acceptable salt thereof, and treating or preventing vasomotor symptoms as described herein includes decreasing the core body temperature of a subject, such as a decrease of about 0.5° C. to about 1° C., about 0.5° C. to about 1.5° C., or about 0.5° C. to about 2° C., such as up to 0.5° C., up to 1° C., up to 1.5° C., or up to 2° C., or any number in between.

Further, for example, the TRPM8 antagonist may be chosen from amide compounds. In some embodiments, the amide compound is represented by the following formula:

[Chem.7]

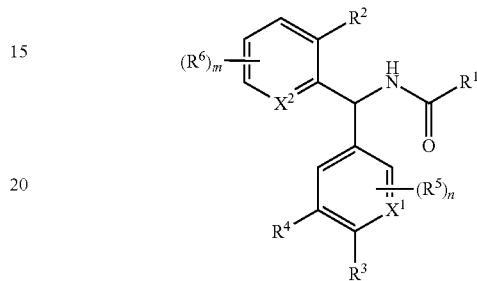

a pharmaceutically-acceptable salt thereof, a tautomer thereof, a pharmaceutically-acceptable salt of the tautomer, a stereoisomer thereof, or a mixture thereof,
wherein:
m is 0, 1, 2 or 3;
n is 0 or 1;
$X^1$ is $C(R^4)$;
$X^2$ is N;
$R^1$ is $C_{1-6}$alk or a direct-bonded, $C_{1-2}$alk-linked, $C_{1-2}$alkO-linked, saturated, partially-saturated or unsaturated 3-, 4-, 5-, 6- or 7-membered monocyclic or 7-, 8-, 9-, 10- or 11-membered bicyclic ring containing 0, 1, 2, 3 or 4 heteroatoms selected from N, O and S, but containing no more than one O or S atom, the $C_{1-6}$alk and ring being substituted by 0, 1, 2 or 3 substituents independently selected from halo, oxo, $C_{1-6}$alk, $C_{1-6}$ alkOH, $C_{1-6}$alk-(C=O)$R^a$, $C_{1-6}$alk-C(=O)OR$^a$, $C_{1-4}$haloalk, cyano, nitro, —C(=O)$R^a$, —C(=O)OR$^a$, —C(=O)NR$^a$R$^a$, —C(=NR$^a$)NR$^a$R$^a$, —OR$^a$, —OC(=O)R$^a$, —OC(=O)NR$^a$R$^a$, —OC(=O)N(R$^a$)S(=O)$_2$R$^a$, —OC$_{2-6}$alkNR$^a$R$^a$, —OC$_{2-6}$alkOR$^a$, —SR$^a$, =S, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, —NR$^a$R$^a$, —N(R$^a$)C(=O)R$^a$, —N(R')C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$NR$^a$R$^a$, —NR$^a$C$_{2-6}$alkNR$^a$R$^a$ and —NR$^a$C$_{2-6}$alkOR$^a$, wherein the ring is additionally substituted by 0 or 1 directly bonded, SO$_2$ linked, C(=O) linked or CH$_2$ linked saturated, partially-saturated or unsaturated 3-, 4-, 5-, 6- or 7-membered monocyclic ring containing 0, 1, 2, 3 or 4 heteroatoms selected from N, O and S, but containing no more than one O or S atom, and substituted by 0, 1, 2 or 3 groups selected from halo, oxo, $C_{1-6}$alk, $C_{1-4}$haloalk, cyano, nitro, —C(=O)R$^a$, —C(=O)OR$^a$, —C(=O)NR$^a$R$^a$, —C(=NR$^a$)NR$^a$R$^a$, —OR$^a$, —OC(=O)R$^a$, —SR$^a$, —S(=O)R$^a$, —S(=O)$_2$R$^a$, —S(=O)$_2$NR$^a$R$^a$, —NR$^a$R$^a$, and —N(R$^a$)C(=O)R$^a$;
$R^2$ is —F or —CF$_3$;
$R^3$ is —OCF$_3$ or —CF$_3$;
$R^4$ is independently, at each instance, H, $C_{1-6}$alk, —C$_{1-3}$haloalk, —OC$_{1-6}$alk, —OC$_{1-3}$haloalk, —N(C$_{1-6}$alk)C$_{1-6}$alk, —NHC$_{1-6}$alk, —NC(=O)C$_{1-6}$alk, —N(C$_{1-6}$alk)C$_{1-6}$alk, F, Cl, Br, CN, OH or NH$_2$; or $R^3$ and $R^4$ together form a four-atom unsaturated bridge containing 0 or 1 N atoms, wherein the bridge is substituted by 0, 1 or 2 $R^5$ substituents;

$R^5$ is independently, in each instance, halo, $OR^a$, $CH_3$ or $CF_3$;

$R^6$ is F, $C_{1-6}$alk, or $OR^a$;

$R^a$ is independently, at each instance, H or $R^b$; and $R^b$ is independently, at each instance, phenyl, benzyl or $C_{1-6}$alk, the phenyl, benzyl and $C_{1-6}$alk being substituted by 0, 1, 2 or 3 substituents selected from halo, oxo, $C_{1-4}$alk, $C_{1-3}$haloalk, —$OC_{1-4}$alk, —OH, —$NH_2$, —$OC_{1-4}$alk, —$OC_{1-4}$haloalk, —$NHC_{1-4}$alk, and —$N(C_{1-4}alk)C_{1-4}$alk.

In certain embodiments, the amide compound is selected from the group consisting of:

(S)-N-((3-fluoro-4-(trifluoromethoxy)phenyl)(3-fluoropyridin-2-yl)methyl)-6-oxo-1,6-dihydropyridine-3-carboxamide;

(S)-N-((3-fluoro-4-(trifluoromethoxy)phenyl)(3-(trifluoromethyl)pyridin-2-yl)methyl)-6-oxo-1,6-dihydropyridine-3-carboxamide;

(S)-N-((2-fluoro-4-(trifluoromethoxy)phenyl)(3-fluoropyridin-2-yl)methyl)-6-oxo-1,6-dihydropyridine-3-carboxamide;

(S)-5-fluoro-N-((3-fluoro-4-(trifluoromethoxy)phenyl)(3-fluoropyridin-2-yl)methyl)-6-oxo-1,6-dihydropyridine-3-carboxamide;

(S)-N-((3-fluoro-4-(trifluoromethyl)phenyl)(3-fluoropyridin-2-yl)methyl)-6-oxo-1,6-dihydropyridine-3-carboxamide;

(S)-6-(((3-fluoro-4-(trifluoromethoxy)phenyl)(3-fluoropyridin-2-yl)methyl)carbamoyl)nicotinic acid;

a pharmaceutically-acceptable salt thereof, a tautomer thereof, a pharmaceutically-acceptable salt of the tautomer, and a mixture thereof.

In some embodiments, the TRPM8 antagonist is chosen from sulfonamide compounds, such as those of formula (I), such as Compound A or a pharmaceutically acceptable salt thereof, and the effective amount for oral administration is chosen from about 0.01 to about 100 mg/kg per day, such as from about 0.1 to about 10 mg/kg per day or any amount in between. In some embodiments, the TRPM8 antagonist is chosen from sulfonamide compounds, such as those of formula (I), such as Compound A, and the effective amount for oral administration is from about 10 mg to about 400 mg, for example, from about 10 mg to about 400 mg per day. The effective amount of the TRPM8 antagonist can vary and may depend on a number of factors, such as the specific active agent, the type of composition or dosage form, the selected route of administration, and the subject under treatment, including factors such as age, weight, sex, and medical condition of the subject.

In some embodiments, the TRPM8 antagonist is chosen from sulfonamide compounds, such as those of formula (I), such as Compound A or a pharmaceutically acceptable salt thereof, and the effective amount of the TRPM8 antagonist or composition thereof is administered on an as-needed basis, such as immediately upon sensing the onset of vasomotor symptoms, such as a hot flash, or in an ongoing dosing regimen. In some embodiments, the TRPM8 antagonist is chosen from sulfonamide compounds, such as those of formula (I), such as Compound A or a pharmaceutically acceptable salt thereof, and the effective amount of the TRPM8 antagonist or composition thereof is administered daily, for example, once daily, such as once daily in the evenings. In some embodiments, the effective amount of a TRPM8 antagonist or composition thereof is administered daily, such as once daily. In some embodiments, the TRPM8 antagonist is chosen from sulfonamide compounds, such as those of formula (I), such as Compound A or a pharmaceutically acceptable salt thereof, and the timing and frequency of administration is chosen to target the treatment or prevention of vasomotor symptoms (e.g., hot flashes) that occur at night (i.e., night sweats) as described herein.

One or more additional active agents may be administered with the TRPM8 antagonist, such as in a combination therapy. Administration of the different active agents may be carried out in a single composition, by concurrent administration of the different active agents in different compositions, or by sequential administration of the different active agents.

Examples of additional active agents include, but are not limited to, active agents for treating or preventing vasomotor symptoms or useful for treatment of other signs and symptoms of hormonal variation, such as estrogen, estrogen receptor modulator, estrogen agonist, androgen receptor modulator, peptide hormone, sedative, hypnotic, anxiolytic, antipsychotic, antianxiety agent, minor tranquilizers, benzodiazepine, barbiturate, serotonin (5-HT) agonist, selective serotonin reuptake inhibitor (SSRI's), 5HT-2 antagonist, non-steroidal anti-inflammatory drug, oral contraceptive, progesterone, progestin, monoamine oxidase inhibitor, carbohydrate mixture and the like, or physical method such as a cooling agent. Further examples of additional active agents include, but are not limited to, estrogen, progesterone, clonidine, venlafaxine, megestrol acetate, mirtazapine, a nonsteroidal anti-inflammatory, such as acetaminophen, alprostadil, aspirin, diclofenac, etodolac, ibuprofen, indomethacin, ketoprofen, ketorolac tromethamine, misoprostol, nabumetone, naproxen, naproxen sodium, oxaprozin, piroxicam, spironolactone, spironolactone with hydrochlorothiazide, or trovafloxacin; a corticosteroid; a selective cyclooxygenase-2 inhibitor, such as celecoxib, etoricoxib, parecoxib, rofecoxib, valdecoxib, meloxicam, flosulide, nimesulide, MK-663, NS 398, DuP 697, SC-58125, SC-58635, or RS 57067, adinazolam, abiraterone, allobarbital, alonimid, alprazolam, amitriptyline, amobarbital, amoxapine, anastrozole, bentrazepam, benzoctamine, bicalutamide, brotizolam, bupropion, buserelin, buspirone, butabarbital, butalbital, capuride, carbocloral, chloral betaine, chloral hydrate, chlordiazepoxide, clomethorone, clomipramine, cloperidone, clorazepate, clorethate, clozapine, cyprazepam, degarelix, delmadinone, desipramine, deslorelin, dexclamol, diazepam, dichloralphenazone, divalproex, diphenhydramine, doxepin, droloxifene, estazolam, estradiol, estrogen, ethchlorvynol, etomidate, exemestane, fadrozole, fenobam, flunitrazepam, flurazepam, flutamide, fluvoxamine, fluoxetine, formestane, fosazepam, fulvestrant, glutethimide, goserelin, halazepam, histrelin, hydroxyzine, idoxifene, imipramine, lasofoxifene, leuprolide, lithium, letrozol, leucine, leuprolide, leuprorelin, lorazepam, lormetazepam, maprotiline, mecloqualone, melatonin, mephobarbital, meprobamate, methaqualone, midaflur, midazolam, nafarelin, nafoxidine, nefazodone, nitromifene, nilutamide, nisobamate, nitrazepam, nociceptin, nortriptyline, ormeloxifene, oxazepam, paraldehyde, paroxetine, pentobarbital, perlapine, perphenazine, phenelzine, phenobarbital, prazepam, progesterone, promethazine, propofol, protriptyline, quazepam, raloxifene, reclazepam, roletamide, secobarbital, sertraline, suproclone, tamoxifene, temazepam, thioridazine, toremifene, tracazolate, tranylcypromaine, trazodone, trioxifene, triazolam, triptorelin, trepipam, tricetamide, triclofos, trifluoperazine, trimetozine, trimipramine, uldazepam, valproate, venlafaxine, vorozole, zaleplon, zolazepam, zolpidem, and salts thereof, and combinations thereof, and the like, as well as admixtures and combinations thereof. Further examples of additional active agents include, but are not limited to, selective estrogen receptor antagonists including tamoxifen (Nolvadex (registered trademark)), raloxifene (Evista (registered trademark)), and toremifene (Fareston (registered trademark)); antiestrogen drugs including fulvestrant (Faslodex (registered trademark)); aromatase inhibitors including anastrozole (Arimidex (registered trademark)), letrozole (Femara (registered trademark)) and exemestane (Aromasin (registered trademark)); Luteinizing-hormone-releasing hormone (LHRH) agonists including goserelin (Zoladex (registered trademark)), leuprolide (Lupron (registered trademark)); Luteinizing hormone (LH) blockers including buserelin, leuprorelin (Prostap (registered trademark)), histrelin (Vantas (registered trademark)) and triptorelin (Decapeptyl (registered trademark)); anti androgens including flutamide (Drogenil (registered trademark)) and bicalutamide (Casodex (registered trademark)); Gonadotrophin releasing hormone (GnRH) blocker including degarelix (Firmagon (registered trademark)); and abiraterone (Zytiga (registered trademark)).

In some embodiments, the present disclosure includes a composition comprising an effective amount of a TRPM8 antagonist for treating or preventing vasomotor symptoms and a pharmaceutically acceptable carrier. In certain embodiments, the composition is a pharmaceutical composition. The composition can be used with an inert carrier suitable for each administration method, and can be formulated into conventional preparations (e.g., tablets, granules, capsules, powder, solution, suspension, emulsion, injection, infusion, etc.). As such a carrier, there may be mentioned, for example, a binder (e.g., gum arabic, gelatin, sorbitol, polyvinylpyrrolidone, etc.), an excipient (e.g., lactose, sugar, corn starch, sorbitol, etc.), a lubricant (magnesium stearate, talc, polyethylene glycol, etc.), a disintegrator (e.g., potato starch, etc.) and the like, which are pharmaceutically acceptable. When the composition is used as an injection solution or an infusion solution, it can be formulated by using, e.g., distilled water for injection, physiological saline, an aqueous glucose solution, etc. In certain embodiments, the present disclosure includes a use of a TRPM8 antagonist or a composition comprising the same as an active ingredient for treating or preventing vasomotor symptoms in a subject in need thereof. Also in certain embodiments, the present disclosure includes a use of a TRPM8 antagonist in a preparation of a medicament for treating or preventing vasomotor symptoms.

It is to be understood that the foregoing description as well as the examples which follow are intended to illustrate and not limit the scope of the invention. Other aspects, advantages and modifications within the scope of the invention will be apparent to those skilled in the art to which the invention pertains.

EXAMPLES

Example 1: Evaluation of TRPM8 Antagonist on Core Body Temperature in Rats

Methods: Compound A (0.3 and 3 mg/kg) or vehicle was orally administered to naive SD rats (n=6). Rectal temperature was measured before, 1, 2, 3 and 6 hours after administration. AUC for 0 to 6 hours was calculated and statistically analyzed.

Results: As shown in FIG. 1, Compound A significantly reduced rectal temperature compared to vehicle (P<0.01). The maximum decrease in rectal temperature was observed at 2 hours after administration of 3 mg/kg and its amplitude was 0.82° C. Rectal temperature before oral administration was between 37.0° C. to 37.8° C.

Example 2: Phase I, Randomized, Double-Blind, Placebo-Controlled Study to Assess the Safety, Tolerability and Pharmacokinetics of Multiple Doses of Compound A in Female Subjects Experiencing Vasomotor Symptoms Study Design: This was a Phase Ib, randomized, double blind, placebo controlled study. The study design is illustrated in FIG. 2. Following the initial Screening visit, eligible subjects was given an actigraphy event monitor (watch) to record episodes of flashing as Vasomotor symptoms (VMS) events during a period of 2 weeks during Screening, in order to confirm VMS eligibility criteria (>7 VMS/day on average during 2 weeks). Subjects may be required to return to the site during the Screening period to read or exchange the actigraphy event monitor. Subjects deemed eligible following review of VMS data were invited to attend the Clinical research unit (CRU) for one residential period of 16 days duration, including 14 days of Investigational Medicinal Product (IMP) administration. Subjects were admitted to the CRU 1 day prior to dosing (Day −1). No medication was administered on Day −1. On Day 1, subjects who meet the study eligibility criteria were randomized to receive one dose level of either Compound A (6 subjects) or a matching placebo (2 subjects) in a double-blind manner. Randomized treatment was administered once nightly, starting on Day 1, for a total duration of 14 days.

The anticipated dose levels of Compound A to be administered is 50 mg for Cohort 1, 200 mg for Cohort 2 and 400 mg for Cohort 3. Progression to the next dose level and selection of the dose to be administered in Cohort 2 and Cohort 3 is based on emerging safety and tolerability data and available core body temperature data from the preceding dose cohort. If the dose escalation stopping criteria are met, then the dose for the subsequent cohort is reduced. The lowest potential dose to be assessed is 10 mg and the maximum dose for the study does not exceed 400 mg. The three cohorts is dosed sequentially with a fourth additional cohort being dosed, if necessary, to investigate other dose levels.

Subjects is discharged from the CRU after all 24 hour post-dose procedures are completed in the evening on Day 15 or in the early morning on Day 16 if deemed more convenient by the subjects, and return for a follow up visit on Day 21. The overall duration of participation for each subject is a maximum of 63 days (from the initial Screening visit on Day −42 to follow-up on Day 21).

Endpoints:
Primary Assessments
  Safety and tolerability: Vital signs, ECG parameters, Clinical laboratory assessments, Physical examination, Adverse events and Assessment of overall tolerability
Secondary Assessments
Pharmacokinetics assessments
Core body temperature assessment
Change from baseline in core body temperature.
Exploratory assessments
Frequency of VMS and sleep assessments.
Mood and subjective sleep quality
Fifty (50) mg of Compound A was administered to the female subjects experiencing Vasomotor Symptoms (VMS), and as the above-mentioned assessments, a Frequency of VMS and a Core body temperature assessment were examined.

For the Frequency of VMS, a change in Mean observed value in Vasomotor Symptoms (VMS) frequency was observed over time within 24-hour after the first dose during the 14 days of treatment period. Here a moderate VMS and a severe VMS were counted as a VMS frequency. The mean observed value in VMS frequency on the each Visit Days are summarized in Table 1.

TABLE 1

| Visit Day | Mean Observed Value | |
|---|---|---|
| | Placebo | Compound A |
| Baseline | 14.8 | 11.2 |
| Day 1 | 13.5 | 11.7 |
| Day 2 | 11.3 | 6.0 |
| Day 3 | 9.2 | 4.7 |
| Day 4 | 9.3 | 4.7 |
| Day 5 | 9.0 | 2.7 |
| Day 6 | 8.3 | 2.8 |
| Day 7 | 9.8 | 3.0 |
| Day 8 | 7.8 | 3.3 |
| Day 9 | 7.3 | 1.3 |
| Day 10 | 8.3 | 3.2 |
| Day 11 | 8.7 | 2.8 |
| Day 12 | 6.5 | 2.7 |
| Day 13 | 7.0 | 2.3 |
| Day 14 | 8.3 | 2.3 |

Each of the Mean Observed Values in VMS frequency for Placebo and Compound A were plotted as shown in FIG. 3. In the FIG. 3, each of the triangle or square symbol shows the result for 50 mg of Compound A or Placebo, respectively. As shown in FIG. 3, Compound A reduced the frequency of VMS significantly and Compound A had an immediate effect because the reduction effect of VMS frequency was shown at Day 2 or later, namely, within a few days of administration, compared to estrogen or selective Serotonin Reuptake Inhibitor such as Paroxetine.

For the Core body temperature assessment, a change from baseline in core body temperature of the subjects was observed over time within 24 hours post-dose on the Visit 1, 7, 10 or 14. The test results are shown in FIG. 4. Each of square, triangle, open circle, or closed circle symbol shows the results on the Visit Day 1, 7, 10 or 14, respectively. As shown in FIG. 4, Compound A showed reduced the core body temperature significantly.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. A method for treating or preventing one or more vasomotor symptoms in a subject in need thereof, comprising:

administering to the subject an effective amount of a Transient Receptor Potential Melastatin 8 (TRPM8) antagonist, wherein the TRPM8 antagonist is chosen from compounds represented by the following formula (I):

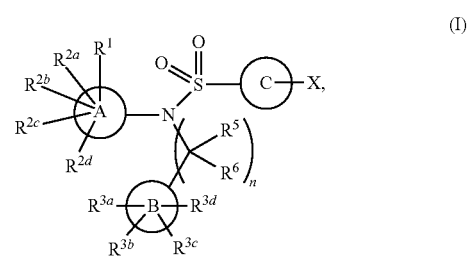

wherein:

Ring A is bicyclic aromatic heterocycle comprised of (a) pyridine condensed with benzene; or (b) pyridine condensed with 5 to 6-membered monocyclic aromatic heterocycle containing carbon atoms and 1 to 4 heteroatoms chosen from oxygen atom, sulfur atom and nitrogen atom, and Ring A binds to a sulfonylamino moiety on a carbon atom adjacent to a nitrogen atom of pyridine ring constituting Ring A, Ring B is chosen from (a) monocyclic or bicyclic aromatic hydrocarbon with 6 to 11 carbons as a ring atom; (b) monocyclic or bicyclic alicyclic hydrocarbon with 3 to 12 carbons as a ring atom; (c) 5 to 11-membered monocyclic or bicyclic aromatic heterocycle containing carbon atoms and 1 to 4 heteroatoms chosen from oxygen atom, sulfur atom and nitrogen atom; and (d) 4 to 12-membered monocyclic or bicyclic non-aromatic heterocycle containing carbon atoms and 1 to 4 heteroatoms chosen from oxygen atom, sulfur atom and nitrogen atom, Ring C is chosen from (a) benzene; and (b) 5 to 6-membered monocyclic aromatic heterocycle containing carbon atoms and 1 to 4 heteroatoms chosen from oxygen atom, sulfur atom and nitrogen atom, $R^1$ is chosen from (a) hydrogen; (b) $C_1$-$C_6$ alkyl which may be optionally substituted by 1 to 7 groups chosen from $C_3$-$C_7$ cycloalkyl, $C_1$-$C_6$ alkoxy, halogen, oxo and hydroxy; (c) $C_3$-$C_7$ cycloalkyl which may be optionally substituted by 1 to 7 groups chosen from $C_1$-$C_6$ alkyl, $C_1$-$C_6$ alkoxy and halogen; (d) $C_1$-$C_6$ alkoxy which may be optionally substituted by 1 to 7 groups chosen from $C_3$-$C_7$ cycloalkyl, $C_1$-$C_6$ alkoxy, halogen and hydroxy; (e) phenyl which may be optionally substituted by 1 to 3 groups chosen from $C_1$-$C_6$ alkyl, $C_1$-$C_6$ halogenoalkyl, $C_3$-$C_7$ cycloalkyl, $C_3$-$C_7$ halogenocycloalkyl, $C_1$-$C_6$ alkoxy, $C_1$-$C_6$ halogenoalkoxy and halogen; (f) halogen; and (g) nitrile, $R^{2a}$, $R^{2b}$, $R^{2c}$ and $R^{2d}$ are each independently chosen from (a) hydrogen; (b) $C_1$-$C_6$ alkyl which may be optionally substituted by 1 to 7 groups chosen from $C_1$-$C_6$ alkoxy, $C_3$-$C_7$ cycloalkyl, halogen, oxo and hydroxy; (c) $C_3$-$C_7$ cycloalkyl which may be optionally substituted by 1 to 7 groups chosen from $C_1$-$C_6$ alkyl, $C_1$-$C_6$ alkoxy and halogen; (d) $C_1$-$C_6$ alkoxy which may be optionally substituted by 1 to 7 groups chosen from $C_1$-$C_6$ alkoxy, $C_3$-$C_7$ cycloalkyl and halogen; (e) phenyl which may be optionally substituted by 1 to 3 groups chosen from $C_1$-$C_6$ alkyl, $C_1$-$C_6$ halogenoalkyl, $C_3$-$C_7$ cycloalkyl, $C_3$-$C_7$ halogenocycloalkyl, $C_1$-$C_6$ alkoxy, $C_1$-$C_6$ halogenoalkoxy and halogen; (f) 5 to 6-membered monocyclic aromatic heterocyclic group which may be optionally substituted by 1 to 3 groups chosen from $C_1$-$C_6$ alkyl, $C_1$-$C_6$ halogenoalkyl, $C_3$-$C_7$ cycloalkyl, $C_3$-$C_7$ halogenocycloalkyl, $C_1$-$C_6$ alkoxy, $C_1$-$C_6$ halogenoalkoxy and halogen; (g) 4 to 7-membered monocyclic non-aromatic heterocyclic group which may be optionally substituted by 1 to 3 groups chosen from $C_1$-$C_6$ alkyl, $C_1$-$C_6$ halogenoalkyl, $C_3$-$C_7$ cycloalkyl, $C_3$-$C_7$ halogenocycloalkyl, $C_1$-$C_6$ alkoxy, $C_1$-$C_6$ halogenoalkoxy and halogen; (h) halogen; and (i) nitrile, $R^{3a}$, $R^{3b}$, $R^{3c}$ and $R^{3d}$ are each independently chosen from (a) hydrogen; (b) $C_1$-$C_6$ alkyl which may be optionally substituted by 1 to 7 groups chosen from $C_3$-$C_7$ cycloalkyl, $C_3$-$C_7$ halogenocycloalkyl (in which the cycloalkyl and halogenocycloalkyl may be each independently optionally substituted by 1 to 3 groups chosen from $C_1$-$C_6$ alkyl and $C_1$-$C_6$ halogenoalkyl), $C_1$-$C_6$ alkoxy, $C_1$-$C_6$ halogenoalkoxy, phenyl, 5 to 6-membered monocyclic aromatic heterocyclic group, 4 to 7-membered monocyclic non-aromatic heterocyclic group (in which the phenyl, aromatic heterocyclic group and non-aromatic heterocyclic group may be each independently optionally substituted by 1 to 3 groups chosen from $C_1$-$C_6$ alkyl, $C_1$-$C_6$ halogenoalkyl, $C_3$-$C_7$ cycloalkyl, $C_3$-$C_7$ halogenocycloalkyl, $C_1$-$C_6$ alkoxy, $C_1$-$C_6$ halogenoalkoxy and halogen), halogen, oxo and hydroxy; (c) $C_3$-$C_7$ cycloalkyl which may be optionally substituted by 1 to 7 groups chosen from $C_1$-$C_6$ alkyl, $C_1$-$C_6$ halogenoalkyl, $C_1$-$C_6$ alkoxy, $C_1$-$C_6$ halogenoalkoxy, halogen and hydroxy; (d) $C_1$-$C_6$ alkoxy which may be optionally substituted by 1 to 7 groups chosen from $C_3$-$C_7$ cycloalkyl, $C_3$-$C_7$ halogenocycloalkyl (in which the cycloalkyl and halogenocycloalkyl may be each independently optionally substituted by 1 to 3 groups chosen from $C_1$-$C_6$ alkyl and $C_1$-$C_6$ halogenoalkyl), $C_1$-$C_6$ alkoxy, $C_1$-$C_6$ halogenoalkoxy, phenyl, 5 to 6-membered monocyclic aromatic heterocyclic group, 4 to 7-membered monocyclic non-aromatic heterocyclic group (in which the phenyl, aromatic heterocyclic group and non-aromatic heterocyclic group may be each independently optionally substituted by 1 to 3 groups chosen from $C_1$-$C_6$ alkyl, $C_1$-$C_6$ halogenoalkyl, $C_3$-$C_7$ cycloalkyl, $C_3$-$C_7$ halogenocycloalkyl, $C_1$-$C_6$ alkoxy, $C_1$-$C_6$ halogenoalkoxy and halogen), halogen and hydroxy; (e) $C_3$-$C_7$ cycloalkoxy which may be optionally substituted by 1 to 7 groups chosen from $C_1$-$C_6$ alkyl, $C_1$-$C_6$ halogenoalkyl, $C_1$-$C_6$ alkoxy, $C_1$-$C_6$ halogenoalkoxy, halogen and hydroxy; (f) phenyl which may be optionally substituted by 1 to 3 groups chosen from $C_1$-$C_6$ alkyl, $C_1$-$C_6$ halogenoalkyl, $C_3$-$C_7$ cycloalkyl, $C_3$-$C_7$ halogenocycloalkyl, $C_1$-$C_6$ alkoxy, $C_1$-$C_6$ halogenoalkoxy and halogen; (g) 5 to 6-membered monocyclic aromatic heterocyclic group which may be optionally substituted by 1 to 3 groups chosen from $C_1$-$C_6$ alkyl, $C_1$-$C_6$ halogenoalkyl, $C_3$-$C_7$ cycloalkyl, $C_3$-$C_7$ halogenocycloalkyl, $C_1$-$C_6$ alkoxy, $C_1$-$C_6$ halogenoalkoxy and halogen; (h) 4 to 7-membered monocyclic non-aromatic heterocyclic group which may be optionally substituted by 1 to 3 groups chosen from $C_1$-$C_6$ alkyl, $C_1$-$C_6$ halogenoalkyl, $C_3$-$C_7$ cycloalkyl, $C_3$-$C_7$ halogenocycloalkyl, $C_1$-$C_6$ alkoxy, $C_1$-$C_6$ halogenoalkoxy and halogen; (i) phenoxy which may be optionally substituted by 1 to 3 groups chosen from $C_1$-$C_6$ alkyl, $C_1$-$C_6$ halogenoalkyl, $C_3$-$C_7$ cycloalkyl, $C_3$-$C_7$ halogenocycloalkyl, $C_1$-$C_6$ alkoxy, $C_1$-$C_6$ halogenoalkoxy and halogen; (j) halogen; and (k) hydroxy, or two substituent groups chosen from $R^{3a}$, $R^{3b}$, $R^{3c}$ and $R^{3d}$ to combine with each other to form oxo, $R^5$ and $R^6$ are each independently chosen from (a) hydrogen; (b) $C_1$-$C_6$ alkyl; (c) $C_1$-$C_6$ halogenoalkyl; (d) $C_3$-$C_7$ cycloalkyl; and (e) $C_3$-$C_7$ halogenocycloalkyl, or $R^5$ and $R^6$ combine each other at their terminals together with the adjacent carbon atom to form 3 to 7-membered monocyclic alicyclic hydrocarbon, n is 0, 1 or 2;

X is chosen from (a) carboxy; (b) $C_1$-$C_6$ alkoxycarbonyl; (c) hydroxy-$C_1$-$C_6$ alkyl; (d) aminocarbonyl wherein a nitrogen atom may be optionally substituted by one group chosen from $C_1$-$C_6$ alkyl, $C_1$-$C_6$ alkoxy and nitrile; and (e) $C_2$-$C_7$ alkanoyl which may be optionally substituted by 1 to 3 halogens;

or a pharmaceutically acceptable salt thereof;

wherein the subject is a human subject.

2. The method of claim 1, wherein the human subject is a menopausal woman.

3. The method of claim 2, wherein the human subject is a perimenopausal woman.

4. The method of claim 2, wherein the human subject is a postmenopausal woman.

5. The method of claim 1, wherein the human subject is a cancer patient.

6. The method of claim 1, wherein the human subject is undergoing or has undergone treatment for cancer.

7. The method of claim 6, wherein the treatment for cancer is gonadal ablative therapy or gonadal hormonal suppressive therapies.

8. The method of claim 1, wherein the human subject has undergone surgery.

9. The method of claim 8, wherein the surgery is hysterectomy, oophorectomy, or orchiectomy.

10. The method of claim 1, wherein the one or more vasomotor symptoms are hot flashes.

11. The method of claim 1, wherein the one or more vasomotor symptoms are night sweats.

12. The method of claim 1, wherein the TRPM8 antagonist is administered upon the onset of the one or more vasomotor symptoms.

13. The method of claim 1, wherein the TRPM8 antagonist is administered daily.

14. The method of claim 13, wherein the TRPM8 antagonist is administered once daily.

15. The method of claim 13, wherein the TRPM8 antagonist is administered twice daily.

16. The method of claim 1, wherein the administration to the human subject of the effective amount of the TRPM8 antagonist decreases the human subject's core body temperature by about 0.5° C. to about 2° C.

17. The method of claim 1, wherein the TRPM8 antagonist is selected from the group consisting of:
  4-({(1-cyclopropyl-4-methylisoquinolin-3-yl)[4-(trifluoromethoxy)benzyl]amino}sulfonyl)benzoic acid,
  4-({(1-isopropyl-4-methylisoquinolin-3-yl)[4-(trifluoromethoxy)benzyl]amino}sulfonyl)benzoic acid,
  4-{[{3-chloro-4-[cyclopropyl(difluoro)methyl]benzyl}(4-methylisoquinolin-3-yl)amino]sulfonyl}benzoic acid,
  4-({(4-cyclopropylisoquinolin-3-yl)[4-(trifluoromethoxy)benzyl]amino}sulfonyl)benzoic acid,
  4-{[{3-chloro-4-[cyclopropyl(difluoro)methyl]benzyl}(1-cyclopropyl-4-methylisoquinolin-3-yl)amino]sulfonyl}benzoic acid,
  4-{[{4-[cyclopropyl(difluoro)methyl]-3-fluorobenzyl}(4-methylisoquinolin-3-yl)amino]sulfonyl}benzoic acid,
  4-({[4-(trifluoromethoxy)benzyl][4-(trifluoromethyl)isoquinolin-3-yl]amino}sulfonyl)benzoic acid,
  4-[((4-cyclopropylisoquinolin-3-yl){5-(trifluoromethyl)pyridin-2-yl]methyl}amino)sulfonyl]benzoic acid, 4-{[{4-[cyclopropyl(difluoro)methyl]-3-fluorobenzyl}(4-cyclopropylisoquinolin-3-yl)amino]sulfonyl}benzoic acid, and a pharmaceutically acceptable salt thereof.

18. The method of claim 1, wherein the TRPM8 antagonist is administered with an additional active agent.

* * * * *

UNITED STATES PATENT AND TRADEMARK OFFICE
CERTIFICATE OF CORRECTION

PATENT NO. : 10,993,939 B2
APPLICATION NO. : 16/308932
DATED : May 4, 2021
INVENTOR(S) : Joseph M. Palumbo It is certified that error appears in the above-identified patent and that said Letters Patent is hereby corrected as shown below:

On the Title Page

Item (73), Assignee: "Mitsubishi Tanabe Pharmaceutical Company, Osaka (JP)" should read
-- Mitsubishi Tanabe Pharma Company, Osaka (JP) --.

Signed and Sealed this
Ninth Day of August, 2022

*Katherine Kelly Vidal*

Katherine Kelly Vidal
*Director of the United States Patent and Trademark Office*